United States Patent [19]

Noma et al.

[11] 4,164,655

[45] Aug. 14, 1979

[54] APPARATUS FOR MEASURING QUANTITY OF ASPHALT INGREDIENT IN AN ASPHALT COMPOUND

[75] Inventors: Ichiro Noma, Osaka; Kazuo Taniguchi, Hirakata, both of Japan

[73] Assignee: Noma Komuten Company Limited, Osaka, Japan

[21] Appl. No.: 865,964

[22] Filed: Dec. 30, 1977

[51] Int. Cl.² ............................................. G01N 23/00
[52] U.S. Cl. ............................... 250/436; 250/432 R; 250/359
[58] Field of Search ............... 250/358, 359, 432, 433, 250/434, 436

[56] References Cited

U.S. PATENT DOCUMENTS

| | | |
|---|---|---|
| 3,148,971 | 9/1964 | MacDonald et al. ............ 250/358 R |
| 3,445,651 | 5/1969 | Starnes ................................ 250/359 |
| 3,678,268 | 7/1972 | Reim et al. ........................ 250/358 R |

Primary Examiner—Bruce C. Anderson
Attorney, Agent, or Firm—Koda and Androlia

[57] ABSTRACT

An apparatus for measuring the quantity of asphalt ingredient in an asphalt compound in an apparatus for mixing asphalt ingredient and an aggregate to form the asphalt compound including a neutronic line which reacts with a hydrogen atom of the asphalt ingredient in such a manner as to decrease the energy in the neutronic line so as to detect the quantity of asphalt ingredient in the asphalt compound, a continuous conveying means for supplying asphalt compound to the neutronic line and a means responsive to the neutronic line for automatically adjusting the amount of asphalt ingredient in the asphalt compound whereby the amount of asphalt ingredient in the asphalt compound is maintained at a standard value.

12 Claims, 12 Drawing Figures

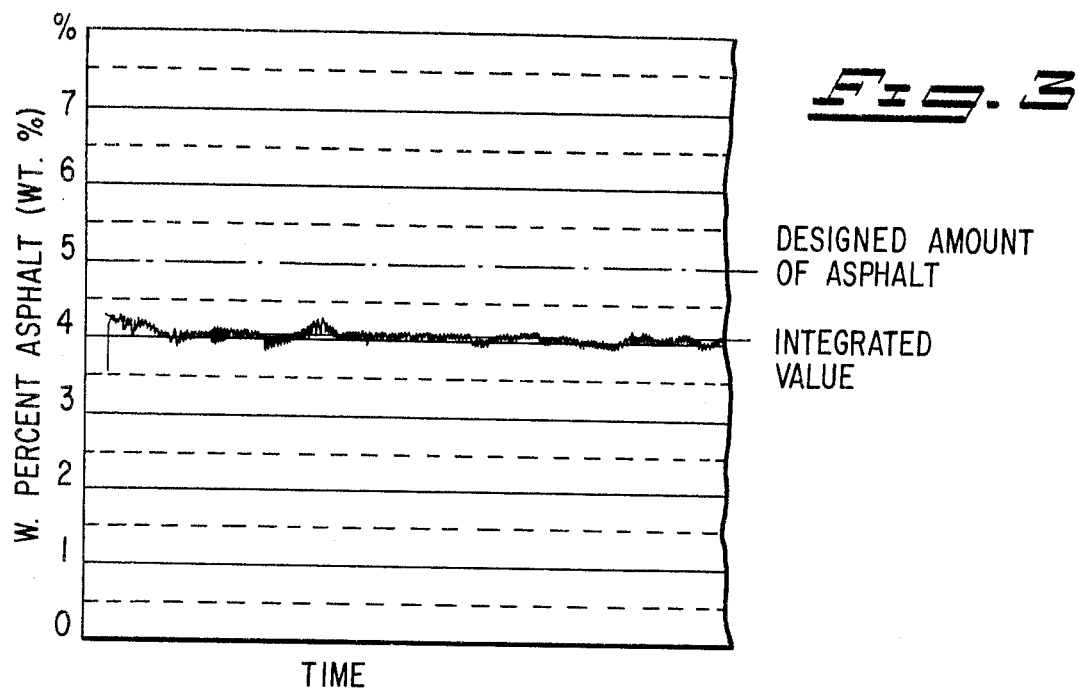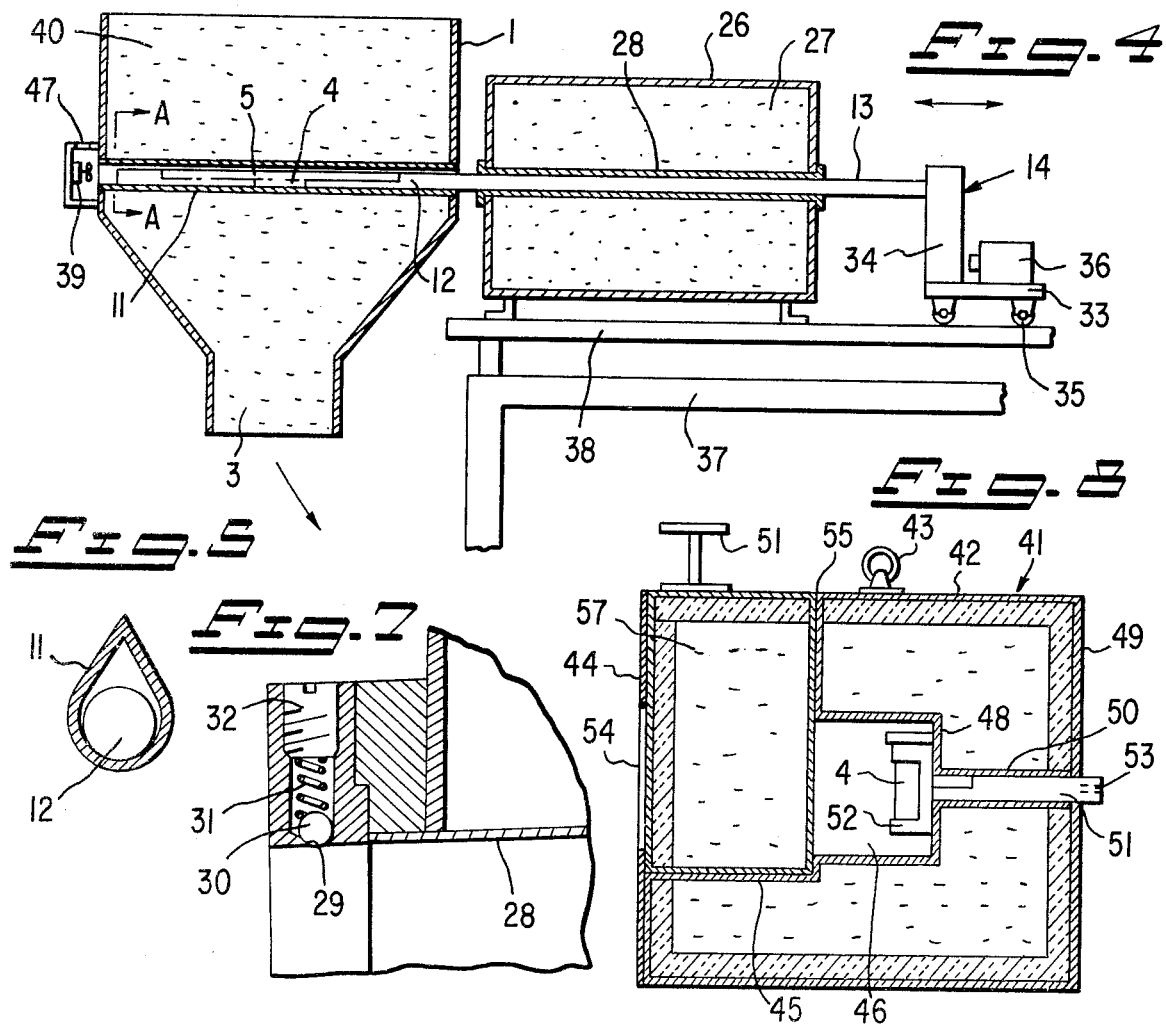

APPARATUS FOR MEASURING QUANTITY OF ASPHALT INGREDIENT IN AN ASPHALT COMPOUND

BACKGROUND OF THE INVENTION

1. Field of the Invention

This invention relates to means for measuring a quantity of asphalt ingredient in an asphalt compound and more particularly to means for checking the amount of asphalt ingredient mixed into an asphalt compound within predetermined limits.

2. Prior Art

Generally to produce asphalt compound, uniform crushed stone and asphalt ingredient are mixed together under heat within a fixed mixture ratio (which is standardized) in proportion to the grades. However, in a practical sense the standard value for the fixed mixture ratio only exists after the asphalt ingredient and the crushed stone are mixed together. Therefore, in the prior art apparatus it has been almost impossible to uniformally control the fixed mixture ratio between the asphalt ingredient and crushed stone in the asphalt compound. It has been suggested that a feedback control system could overcome this difficulty but such a system has not been invented or implemented as yet. Additionally, in the prior art apparatuses when the crushed old asphalt compound is reused instead of crushed stone, it is required to measure the amount of asphalt ingredient which is contained in the old asphalt compound prior to introducing it into the apparatus from mixing the asphalt ingredients and the old asphalt compound. Such additional work adds to the steps of manufacture ashpalt compound and increases the cost.

SUMMARY OF THE INVENTION

Accordingly, it is the general object of the present invention to provide a means for accurately measuring the amount of asphalt ingredient in an asphalt compound.

It is another object of the present invention to provide a means for measuring the amount of asphalt ingredient in asphalt compound which can be used in a feedback control system for the production of asphalt compound.

It is yet another purpose of the present invention to provide a means for measuring the amount of asphalt ingredient in an asphalt compound so that old asphalt compound can be effectively used to make a new asphalt compound.

It is still another object of the present invention to provide a means for measuring the amount of asphalt ingredient in an asphalt compound which includes a heating apparatus which heats and dehydrates the asphalt compounds.

In keeping with the principles of the present invention, the objects are accomplished by a unique apparatus for measuring the quantity of the asphalt ingredient in an asphalt compound in an apparatus for mixing asphalt ingredient and an aggregate to form the asphalt compound. The apparatus for measuring the quantity of asphalt ingredient includes a neutronic line which reacts with a hydrogen atom of the asphalt ingredient in such a manner as to decrease the energy in the neutronic line so as to detect the quantity of asphalt ingredient in asphalt compound, a continuous conveying means for supplying asphalt compound to the neutronic line and a means responsive to the neutronic line for automatically adjusting the amount of asphalt ingredient in the asphalt compound whereby the amount of asphalt ingredient in the asphalt compound is maintained at a standard value.

BRIEF DESCRIPTION OF THE DRAWINGS

The above mentioned features and objects of the present invention will become more apparent with references to the following description taken in conjunction with the accompanying drawings, wherein like referenced numerals denote like elements, and in which:

FIG. 3 illustrates the measured results of asphalt content in a regular consecutive conveyance of asphalt compound by plodding the weight percentage versus time;

FIG. 4 illustrates a vertical sectional view showing one embodiment of a measuring apparatus in accordance with the teachings of the present invention;

FIG. 5 illustrates a magnified cross section along the line A—A in FIG. 4;

FIG. 7 illustrates a partial magnified cross section of a safety case in the apparatus of FIG. 4;

FIG. 8 illustrates a vertical sectional view of a conveyance apparatus between the neutronic line resource and the storage room in the present invention;

DETAILED DESCRIPTION OF THE INVENTION

Figure 1:
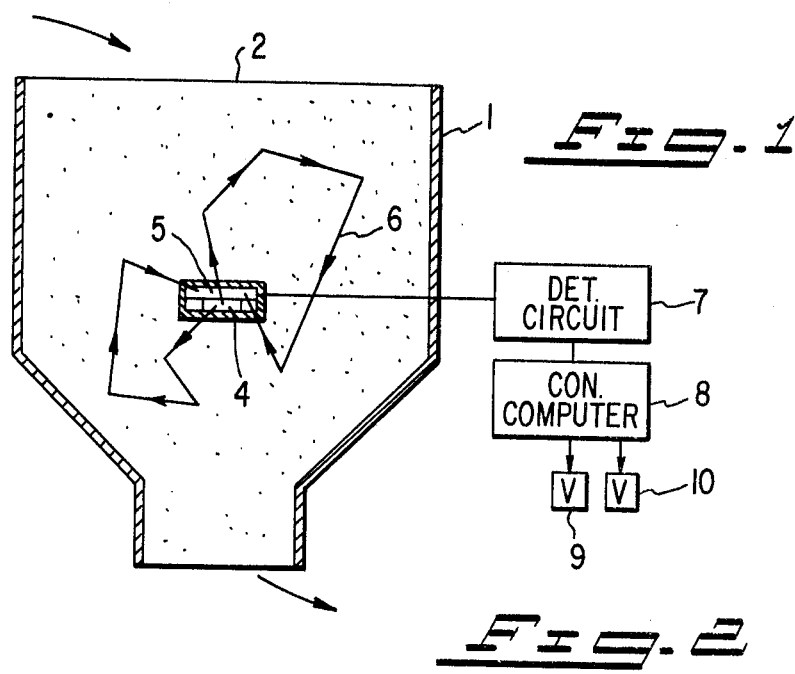
FIG. 1 illustrates one embodiment of a measuring apparatus in accordance with the teachings of the present invention.

Referring more particularly to the Figures, shown in FIG. 1. is a basic embodiment of a measuring apparatus in accordance with the teachings of the present invention. The measuring apparatus in FIG. 1 includes a container 1 formed in a hopper style having upper and lower openings 2 and 3. Asphalt compound flows into the container 1 through the opening 2 and flows out of the opening 3 at a fixed speed and proportion to the weight of the asphalt compound. The container 1 is made of iron and is provided with a neutronic line source 4 and a neutronic line detector 5 at approximately the center thereof. The neutronic line source 4 radiates a rapid neutronic line which has an energy in the mega-electron volt (MeV) level. For instance it would be preferable to utilize a $Am^{2+1}+Be$. Also the neutronic line detector 5 detects the thermal neutronic line in electron volts (eV). For instance it would be desirable to use a $BF_3$ detector or $He^3$ detector.

The rapid neutronic line which is radiated from the line source 4 reacts with the various elements around it, especially the asphalt compound. The amount of the neutronic line activity is illustrated by element 6 in FIG. 1. Then an average decrease in the rate of neutronic line energy is measured as the result of the reaction between the various elements and the electronic line. It is clear that the hydrogen atom has the highest rate of decrease as shown in the following table.

TABLE

| Element | Average Decrease Rate | Element | Average Decrease Rate |
| --- | --- | --- | --- |
| H | 1.000 | P | 0.063 |
| Li | 0.268 | S | 0.061 |
| B | 0.171 | Ce | 0.056 |
| C | 0.158 | K | 0.050 |
| N | 0.136 | Ca | 0.049 |
| O | 0.120 | Ti | 0.041 |
| Na | 0.0084 | Cr | 0.038 |
| Mg | 0.081 | Mn | 0.035 |
| Al | 0.072 | Fe | 0.035 |
| Si | 0.069 | Ni | 0.033 |

Moreover, it is clear from the above table that the thermal neutronic line detected by the detector 5 is mainly produced by the reaction between the neutronic line and the hydrogen atom.

Figure 2:
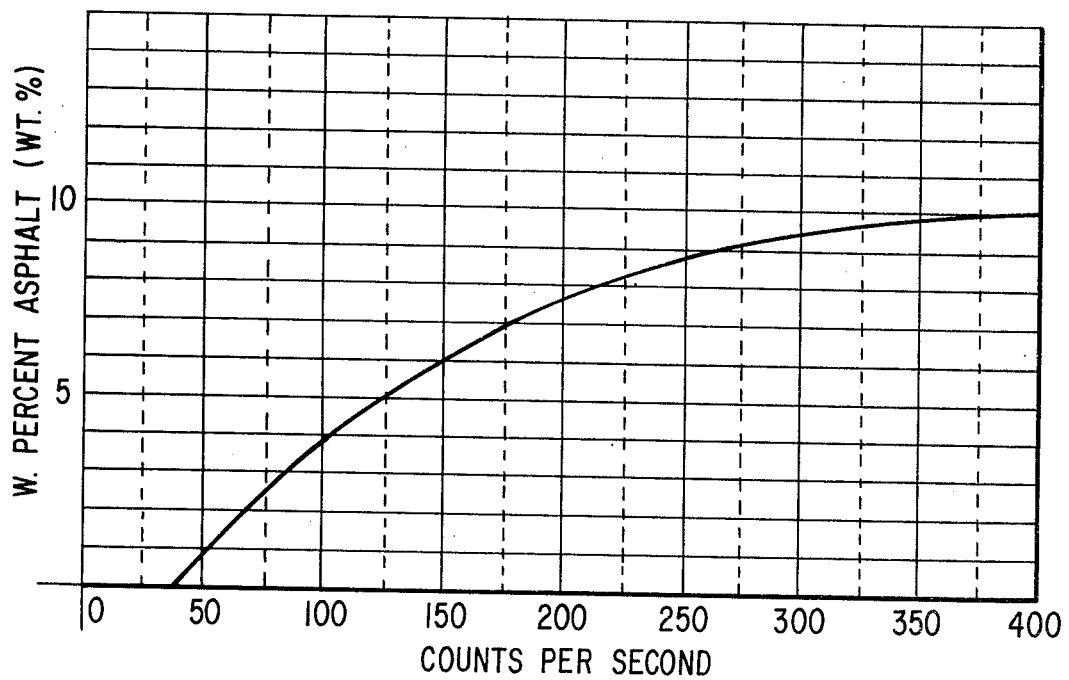
FIG. 2 is a graph illustrating the relationship between a count by the detector and a weight percentage of asphalt ingredient.

It should be noted that hydrogen atoms are only contained in the dehydrated asphalt ingredient ($C_nH_m$) in the asphalt compound and therefore, the detected value of the detector 5 shows the number of hydrogen atoms in the asphalt ingredient. Since the n/m ratio in the chemical formula $C_nH_m$ is a fixed number and can be determined in advance, the mass ratio of the amount of H or C in the asphalt ingredient is fixed. Accordingly, it is possible to plot the quantity of asphalt ingredient against the detected value and the weight percentage in the asphalt compound. FIG. 2 illustrates this result graphically.

In FIG. 2, it is clear that the asphalt weight percentage against the detective value or the counts per second illustrates a gently-sloping curve as the counts incease. The graphic FIG. 3 illustrates the record of the amount of asphalt content (in weight percentage) in a consecutive conveyance process of the asphalt compound in comparison with the curve in FIG. 2. The amount of asphalt content has a uniform allowed range as a standard value. The graphic FIG. 3 illustrates that it is very significant from the stand point of control to compare results with a standard value or to check the excess and deficiency amounts. The detected value from the detector 5 is utilized with a proper electronic circuit 7 and generates a signal as an indication of the weight percentage after a conversion to corresponding quantity and an intergration operation. The detecting circuit of 7 is well known in the prior art and any such circuit could be utilized. For the situation wherein used asphalt compound is utilized instead of a crushed rock, the asphalt ingredient in the old asphalt compound is utilized in the new asphalt compound and by measuring the old asphalt ingredient an insufficiency is counted. By inputing this insufficiency data into a controlled computer 8, the insufficiency amount supply valve 9 and the deoxidizing agent supply bulb 10 are operated to reinforce the viscosity, permeation and endurance and to prevent the degeneration of the asphalt compound.

Referring to FIG. 4, shown therein is a more detailed implementation of a measuring apparatus in accordance with the teachings of the present invention. In FIG. 4, the measuring apparatus includes a protective pipe 11 which extends into the hopper 1 so that it is possible to freely put in and take out the line source 4 and the detector 5. The protective pipe 11 is installed in a side wall of the hopper 1 in a horizontal position but could be installed at any angle. Both ends of the protector pipe 11 extend out of the wall of the hopper 1 and are open.

A vertical cross section of protector pipe 11 is formed as shown in FIG. 5. As shown in FIG. 5, the top side is pointed and the bottom side has an arcuate shape. As a result of the shape, the flow of the asphalt compound toward the bottom of the hopper 1 is smooth. Into the protective pipe 11 is inserted a moving pipe 12 which contains the line source 4 and the detector 5. The outside end of pipe 12 is coupled to a shifting member 14.

Figure 6:
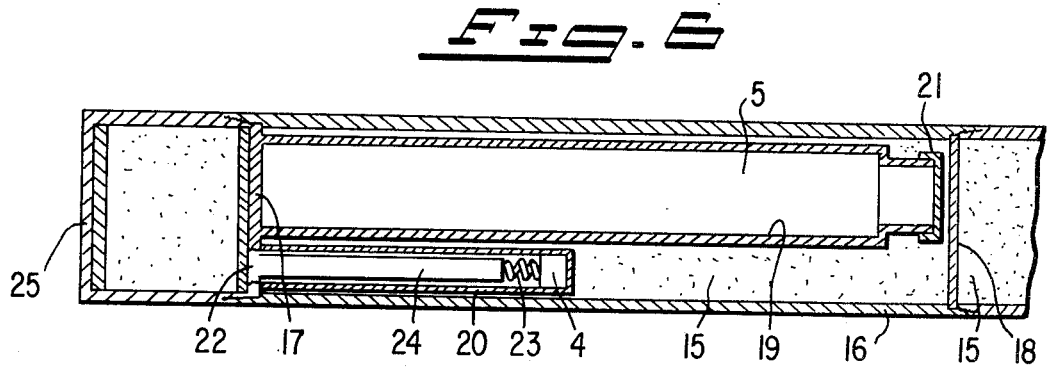
FIG. 6 illustrates a partial magnified vertical sectional profile of a moving pipe in FIG. 4.

The inside end of moving pipe 12 is filled with paraffin 15. The inserted end of moving pipe 12 is provided with a removable receiving pipe 16 which is divided from the remainder of the pipe 12 by a partition 18 located at the coupling point as shown in FIG. 6. A supporting wall 17 is provided on side of receiving pipe 16 and both pipe 19, which contains the detector 5, and pipe 20 which contains the line source 4, are mounted in parallel on supporting wall 17. A cap 21 is provided on the end of detector maintaining pipe 19 to allow for the installation and removal of the neutron detector 5. The line source maintaining pipe 5 has a cover 22 in a female threaded hole on the support wall 17. The neutronic line source 4 is inserted into the end of the line source maintaining pipe 20 and is pressed into the end of the pipe 20 by the piston 24 with a compression spring 23. The female thread of the hole in supporting wall 17 is closed by a lid 22 that holds the other end of piston 24. A sheltered pipe 25 filled with paraffin is coupled to the end of receiving pipe 16.

A safety case 26 simultaneously serving as a guide for the shifting member 14 is provided on the outside of the moving pipe 12. The safety case 26 is a coaxial double pipe made of steel and is filled with paraffin in the middle. Both ends of the internal pipe 28 are provided with a large number of freely revolving ball bearings which project elastically into the end of the pipe 28 so as to insure good movement of the moving pipe 12 through the internal pipe 28.

Referring to FIG. 7, shown therein is the construction of the ends of the internal pipe 28. In particular, a plurality of holes 27 are provided in the ends of pipe 28 and a screw 32 is threaded into each of these holes 27. The holes 27 are such that the end of the hole which projects into the center of the internal pipe is a little narrower than the remainder of the hole. Therefore, the face of the ball 30 provided in the hole 29 projects into the interior of internal pipe 29. The balls 30 are pushed against the narrow portion of the hole 29 by compression spring 31 provided between the ball 30 and the screw 32. In operation the safety case 26 protects the line source 4 from having an influence on the outside world by means of containing the line source 4 in the safety case 26 when the measuring apparatus is not being utilized.

The shifting apparatus 14 consists of a holder 33, a support 34 coupled to the movable pipe 12 and the holder 33, shifting wheels 35 rotatably coupled to the holder 33 and a motor 36 for driving the shifting apparatus 14. The motor 36 drives the wheels 35 and power shifting apparatus 14. By supplying electric power to the motor 36, the shifting apparatus 14 moves thereby causing the pipe 12 to move. The shifting wheels 35 move on the rail 38 which is held by a supporting frame 37 and laid parallel to the moving pipe 12. Therefore, a remote control system is available to move the shifting apparatus 14 a desired distance by utilizing a limit switch (not shown) on the rail 38 and an electric control circuit. The opposite end of protective pipe 11 from the safety case 26 is provided with a fan 39 mounted on a frame 47 which is coupled to an outer wall hopper 1. The fan 39 forces cooling air through the pipe 11 and keeps the detector 5 at about 60°C. or less. The air blown into a protective pipe 11 absorbs the heat generated by the heated asphalt material 40 passing through the hopper 1 and is exhausted from the end of the protective pipe 11. It should be apparent that the fan 39 could be replaced by a blast pipe (not shown). Moreover, as to cooling, the structure of protective pipe 11 shown in FIG. 5 has an additional advantage in that it makes cold air circulate well around the movable pipe 12.

Referring to FIG. 8, shown therein is a conveyance apparatus 41 for the situation wherein it is desirable to convey the line source 4 between the movable pipe 12 and a storage room (not shown). The conveyance apparatus 41 is formed of a holder 43 attached to a wall 42 located in the middle of the apparatus 41 and a space 46 supported by a partition wall 45 projecting from one side wall 44 of the conveyance apparatus 41. This space 46 is opened to a vertical part of partition wall 45. The supporting pipe 50 extends through interior wall 48 of space 46 to wall 49 of the conveyance apparatus 41. A coupling rod 51 is inserted in the supporting pipe 50 and is coupled at one end within the space 46 to a holder 52. One end of the coupling rod 51 sticks out of the side wall 49 and has a coupling screw hole 53 provided in the end thereof. An outtake hole 54 is opened in the side wall 44 of the conveyance apparatus 41 and corresponds to the open hole in the space 46 and a removable outtake room 57 provided with a carrying handle 56 is freely inserted into the space 55 formed between the partition wall 45 and the wall 44.

To take the line source 4 out of the conveyance apparatus 41, the outtake room 57 is extracted from the conveyance apparatus 41 by means of the handle 56 and an operating rod (not illustrated) is connected directly to the coupling screw hole 53 of the projecting rod 51 on the side wall 49 of the container 41. This operating rod is pushed into the supporting pipe 50. The holder 52 containing the line source 4 is moved to the outside container through the opening in the open space 46 and the space 55. Thus, the installation, conveyance and custody of the line source 4 can be done without approaching the line resource 4.

Figure 9:
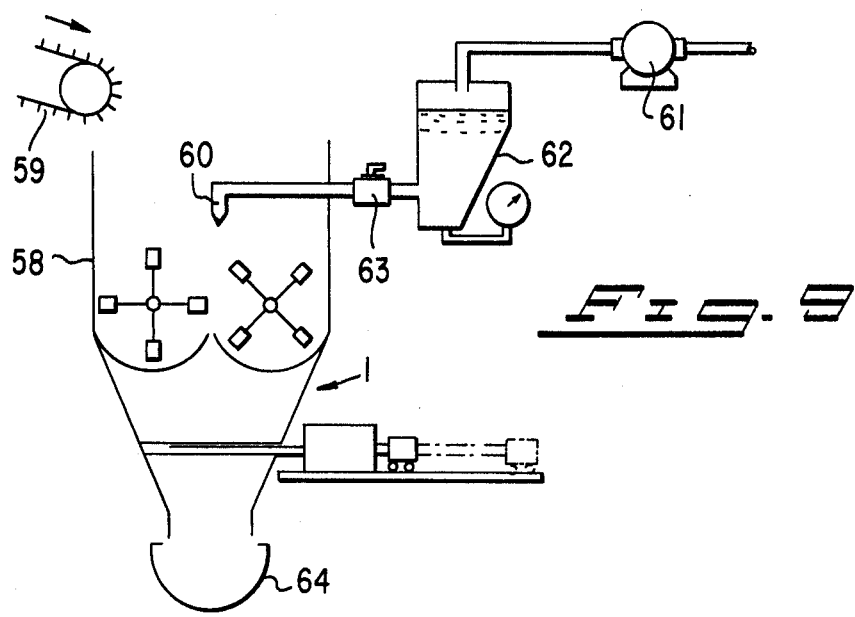
FIG. 9 illustrates an embodiment more in measuring device in accordance with the teachings of the present invention is utilized in asphalt plant of the batch processing type.

Referring to FIG. 9, shown therein is a measuring apparatus in accordance with the teachings of the present invention utilized in a asphalt plant of the batch type. In FIG. 9, a concrete bearer 59, onto which the aggragate such as the crushed rock is carried, and a nozzle 60, from which the asphalt ingredient is dropped, are provided adjacent the opening to a mixer 58. The aggragate is intermittedly dumped into the mixer 58 by the bearer 59 and mixed at a standard fixed mixing rate. The asphalt oil nozzle 60 and a asphalt ingredient tank (not shown) are connected via an oil pipe line, a pump 61, a measuring tank 69 and a stop valve 63.

The measuring apparatus 1 is provided between the mixer 58 and a receiving tank 64. By means of the measuring apparatus 1, the asphalt content rate (weight percentage) is measured consecutively so long as the asphalt compound exists. In this case, if the asphalt content of the asphalt compound varies outside of the permitted range about a standard value, it is considered that the variation occurred in the measuring tank 62. Accordingly, the pump 61 is automatically adjusted by some proper method for the next batch.

Figure 10:
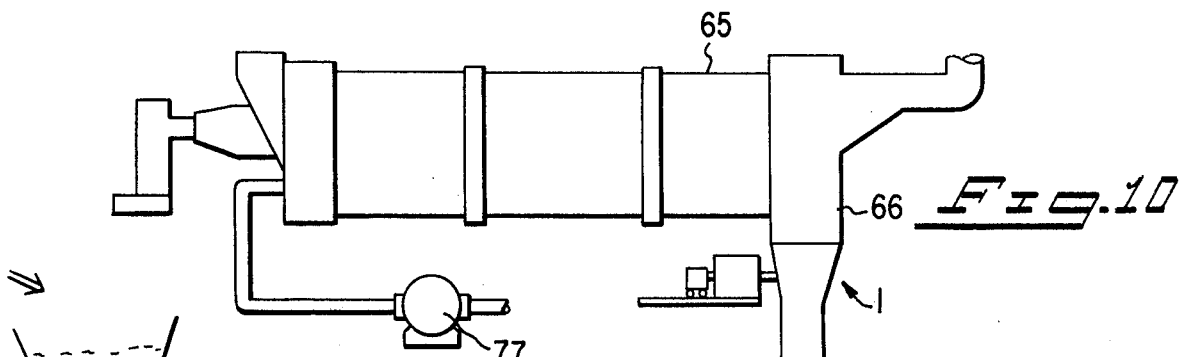
FIG. 10 illustrates another embodiment wherein the measuring device according to the teachings of the present invention utilized in asphalt plant of the drum mixing type.

FIG. 10 illustrates a situation wherein the measuring apparatus of the present invention is utilized in an asphalt plant of the dry mixing type. In this case, the measuring apparatus 1 is provided at an asphalt compound discharge hole 56 in the dry mixer 65. In the previous case or in this case, the measuring apparatus 1 is utilized wherein the asphalt compound is produced. In this drum mixing type asphalt plant, the supplying pump 77 is controlled in proportion to the measurement of the measuring apparatus 1 in the same manner as described in the embodiment above (FIG. 9)

Figure 11:
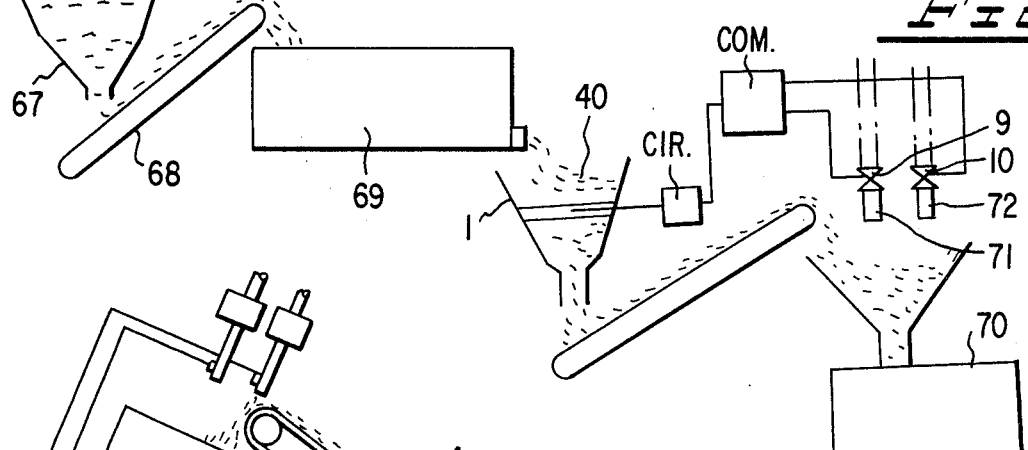
FIG. 11 illustrates another embodiment wherein the measuring apparatus is utilized in a process plant wherein crushed old asphalt compound is reused.

In FIG. 11, shown therein is a situation wherein the measuring apparatus of the present invention is utilized in asphalt plant wherein the asphalt ingredient is contained in crushed old asphalt compound and such old crushed asphalt compound is utilized effectively. In FIG. 11, crushed old asphalt compound is supplied to hopper 67. Bearer 68 carries the crushed old asphalt compound from the end of hopper 67 to heating apparatus 69. Dehydration is done in the heating apparatus 69 and the material 40 containing the used asphalt is then measured by the measuring apparatus 1 and then carried to the mixer 70. At the mixer 70, an aspahlt insufficiency amount supply nozzle 71 and a deoxidizing supply nozzle 72 which are controlled by control valves 9 and 10 are provided. The valves 9 and 10 are controlled by the converted detected value from the detector 5 which is in the form of a voltage or a current by means of the electronic circuit 7 and the computer 8 (see FIG. 1). The valves 9 and 10 are controlled to supply a proper amount of asphalt ingredient and/or deoxidizing agent so that the asphalt compound has the correct amount of asphalt ingredient.

In operation, the asphalt ingredient content is measured by the measuring apparatus 1 and the supply nozzle 71 and the deoxidizing supply nozzle 72 are controlled by valves 9 and 10 in response to the measured data to supply asphalt ingredient and deoxidizing agent to the mixer 70 such that the asphalt compound from the mixer 70 has the proper amount of asphalt ingredient.

Figure 12:
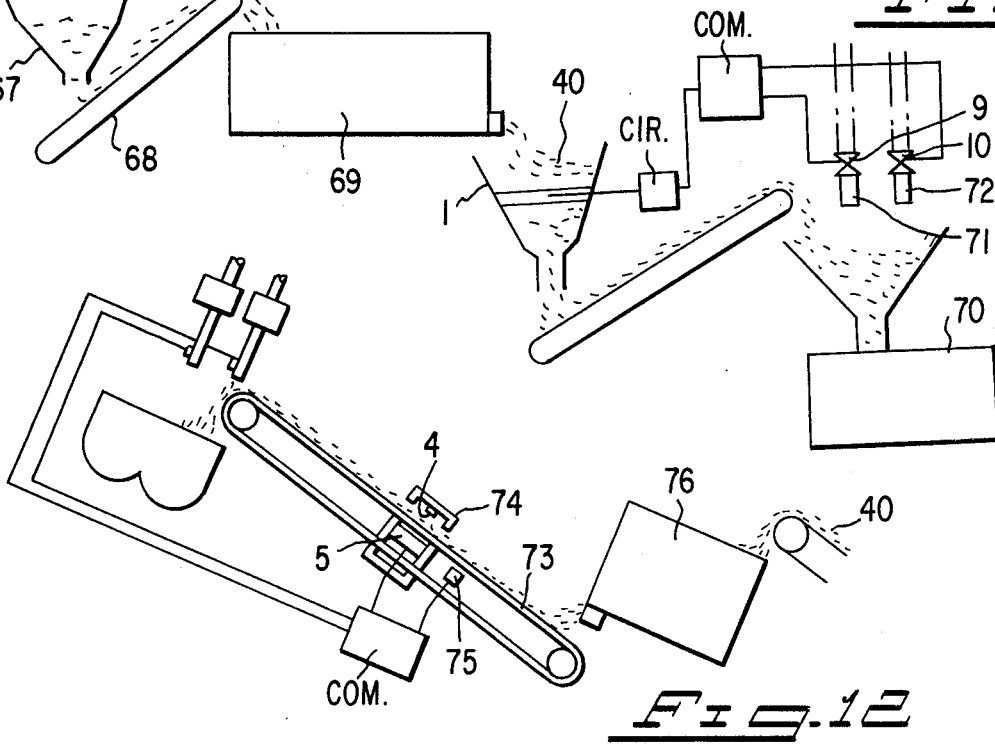
FIG. 12 illustrates still another embodiment wherein the measuring apparatus in accordance with the teachings of the present invention is utilized in a process plant wherein old asphalt compound is reused.

Referring to FIG. 12, shown therein is another asphalt plant utilizing the old asphalt compound. In this arrangement, the neutronic source 4 is provided adjacent a surface of a conveyor 73 which conveys asphalt material 40. The neutron detector 5 is provided adjacent the neutronic source 4 on the undersurface of the conveyor 73. The neutronic source 4 in the detector 5 are surrounded by a protective cover 74. The neutron detector 5 may be installed on the same side as the neutronic source 4 because of the reaction or the dispersal of the radiated neutronic line.

In this asphalt plant which utilizes old asphalt compound, the asphalt compound is heated by a heating apparatus 76. A weighing apparatus 75 is located underneath the surface of the conveyor 73 and the asphalt content amount per weight unit in each part of the conveyed material is measured. The asphalt compound from the conveyor 73 is dumped into a mixer into which a asphalt supply nozzle and a dioxiding agent supply nozzle which are controlled by values which are in turn controlled by a computer which receive data from the detector 5 and the weighing apparatus 75. In this way the proper amount of asphalt ingredient in the asphalt compound produced is maintained.

It should be apparent to one skilled in the art, that the above described embodiment is merely illustrative but a few of the many possible specific embodiments which represents the application of the principles of the present invention. Numerous and varied other arrangements can be readily devised by those skilled in the art without departing from the spirit and scope of the invention.

We claim:

1. An apparatus for measuring the quantity of asphalt ingredient in an asphalt compound in an apparatus for mixing asphalt ingredient and an aggregate to form the asphalt compound comprising:
   a container;
   a means for radiating a neutronic line provided within the container which reacts with a hydrogen atom of said asphalt ingredient in such a manner as to decrease the energy of the neutronic line;
   a detector provided in said container adjacent said radiating means for detecting changes in the energy of said neutronic line;
   a continuous conveying means for continuously supplying asphalt compound into said container; and
   a means responsive to the detector for automatically adjusting the amount of asphalt ingredient in said asphalt compound whereby the amount of asphalt ingredient in said asphalt compound is maintained at a standard value.

2. An apparatus for measuring the quantity of asphalt ingredient contained in an asphalt compound composed of an asphalt and a material, comprising a hopper wherein the asphalt compound flows down vertically at a fixed speed, a penetrating protective pipe extending through a side wall of said hopper, a removable moving pipe provided in said protective pipe, a neutronic line source provided in said removable moving pipe for radiating a neutronic line in the conveyed asphalt compound, a detector provided in said movable moving pipe for detecting a decrease in the energy of the neutronic line caused by reaction with the asphalt and a shifting means for shifting the moving pipe.

3. A measuring apparatus according to claim 2 further comprising means to supply an asphalt and a deoxidizing agent into the asphalt compound when said material is made of crushed asphalt compound.

4. A measuring apparatus according to claim 2, which has a neutronic line source containing an energy to the extent of a mega electron volt, and a neutronic line detector containing an energy to the extent of an electron volt.

5. A measuring apparatus according to claim 4 wherein said source is a 24/Am+Be and said detector is $BF_3$.

6. A measuring apparatus according to claim 4 wherein said source is a 24/AM+Be and said detector is $He^3$.

7. A measuring apparatus according to claim 2 which includes a heating apparatus for the asphalt compound which heats the asphalt compound as it is being conveyed passed the neutronic source.

8. A measuring apparatus according to claim 2 wherein said protective pipe has an acute shape on an upper side and an arc shape on a lower side in a vertical cross-section.

9. A measuring apparatus according to claim 8 further comprising a safety case to guide said moving pipe and to protect from a radiant rays, said safety case being provided adjacent and external to said hopper.

10. A measuring apparatus according to claim 2 further comprising a fan installed on one end of the protective pipe opened to the outside of a side wall of said hopper for the purpose of cooling the neutronic line detector.

11. A measuring apparatus according to claim 2 wherein said conveying means comprises a bearer and the neutronic line source is located on a surface of the bearer at a desired distance and the detector is provided underneath the bearer.

12. A measuring apparatus according to claim 11 further comprising a protective cover about said source and detector, a means for detecting the weight of said material on said bearer and a means responsive to said weight detecting means and said neutronic detector for determining the quantity of asphalt ingredient per unit weight.

* * * * *